United States Patent [19]

Jiang et al.

[11] Patent Number: 4,656,274

[45] Date of Patent: Apr. 7, 1987

[54] POLYFLUORINATED SUBSTITUTED TRICYCLIC QUINOLINE MONO AND DIOXO ANTIFUNGAL AGENTS AND PROCESS FOR THEIR PREPARATION

[75] Inventors: Jack B. Jiang, Wilmington, Del.; David Isaacson, East Brunswick, N.J.

[73] Assignee: Ortho Pharmaceutical Corporation, Raritan, N.J.

[21] Appl. No.: 701,008

[22] Filed: Feb. 12, 1985

[51] Int. Cl.$^4$ .................. C07D 471/04; C07D 219/06
[52] U.S. Cl. ..................................... 544/250; 546/81; 546/102; 546/104
[58] Field of Search ......................... 546/81, 102, 104; 544/250; 514/267

[56] References Cited

U.S. PATENT DOCUMENTS 2,926,166  2/1960  Hitchings et al. .................. 544/250

OTHER PUBLICATIONS

Vasilevskaya, et al., Chemical Abstracts, vol. 75, 98279u (1971).
Gerasimova, et al., Chemical Abstracts, vol. 79, 53161r (1973).
Gerasimova, et al., Chemical Abstracts, vol. 85, 94,262s (1976).
Jiang, et al., J. Heterocyclic Chem, vol. 22, No. 1, pp. 159–160 (1-2/85).

Primary Examiner—Donald G. Daus
Assistant Examiner—Diana G. Rivers
Attorney, Agent, or Firm—Benjamin F. Lambert

[57] ABSTRACT

Polyfluorinated substituted quinoline mono- and dioxo compounds and a method for preparing them are described. The fluorinated oxo compounds are useful as antifungal agents.

6 Claims, No Drawings

POLYFLUORINATED SUBSTITUTED TRICYCLIC QUINOLINE MONO AND DIOXO ANTIFUNGAL AGENTS AND PROCESS FOR THEIR PREPARATION

DESCRIPTION OF THE INVENTION

The present invention relates to polyfluorinated substituted quinoline mono- and dioxo compounds of the formula:

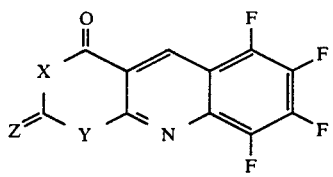

wherein X and Y are each methylene or —NR;
wherein R is lower alkyl having 1-5 carbon atoms, Z is oxo, thioxo, imino and —$(R_1)_2$ wherein $R_1$ is lower alkyl having 1-5 carbon atoms. The novel compounds of this invention are useful as antifungal agents.

The polyfluorinated substituted quinoline mono- and dioxo compounds are prepared by reacting pentafluorobenzaldehyde with an appropriately substituted enaminone in an organic acid. Suitable organic acids which can be employed include acetic acid, propionic acid and butyric acid. The reaction is preferably carried out at the reflux temperature of the mixture. Best results are generally obtained when the reaction is carried out at a temperature between 80° C. and 120° C. The product is separated from the reaction mixture and purified by techniques known to those skilled in the art.

This invention is further disclosed in the following examples of more preferred embodiments thereof, which are presented for the purpose of illustration and not by way of limiting the scope of the invention.

EXAMPLE 1

5,6,7,8-Tetrafluoro-1,3-dimethylpyrimidinol[6,5-b]quinolin-2,4-dione (I)

A mixture of 6-amino-1,3-dimethyluracil (5.0 g; 0.032 mol) and pentafluorobenzaldehyde (6.3 g, 0.032 mol) in glacial acetic acid was heated to reflux under a nitrogen atmosphere for 1 hr. Upon cooling to room temperature, a white crystalline solid precipitated and was collected by filtration, washed with methanol and dried in vacuo at 110° C. for 2 days to give the title compound, yield 8.7 g (87%), mp 227°-228° C.

Ir (potassium bromide), 3060, 1725, 1665, 1615, cm$^{-1}$; $^1$H nmr (trifluoracetic acid): δ9.62 (d, J=1 Hz, 1 H, C-9 H), 4.05 (s, 3 H, N-3 $CH_3$), 3.73 (s, 3 H, n-1 $CH_3$); ms: m/e 313, 201 (B.P.).

When in the above procedure 6-amino-1,3-diethyluracil, 6-amino-1,3-dipropyluracil or 6-amino-1,3-dibutyluracil are employed in place of 6-amino-1,3-dimethyluracil, the corresponding 5,6,7,8-tetrafluoro-1,3-diethylpyrimidino[6,5-b]quinolin-2,4-dione, 5,6,7,8-tetrafluoro-1,3-dipropylpyrimidino[6,5-b]quinolin-2,4-dione and 5,6,7,8-tetrafluoro-1,3-dibutylpyrimidino[6,5-b]quinolin-2,4-dione are obtained.

EXAMPLE 2

5,6,7,8-Tetrafluoro-2,2-dimethylbenzo[2,1-b]quinolin-4-one (II)

A mixture of 3-amino-5,5-dimethyl-2-cyclohexen-1-one (4.2 g, 0.030 mol) and pentafluorobenzaldehyde (6.0 g, 0.030 mol) was heated in glacial acetic acid (30 ml) to reflux for 1 hour under a nitrogen atmosphere. The mixture was cooled to room temperature, concentrated and chromatographed (flash column on silical gel with 2% methanol in methylene chloride) to give the product as a white crystalline solid after recrystallization from methylene chloride/hexanes, yield 4.4 g (50%), mp 150°-154° C.

Ir (potassium bromide) 1690, 1670, 1600, cm$^{-1}$; $^1$H nmr (deuteriochloroform): δ9.05 (b, 1 H, C-10 H), 3.27 (s, 2H, C-3 H), 2.70 (s, 2 H, C-1 H); 1.15 (s, 6 H, two C-2 $CH_3$); ms: m/e 297, 241 (B.P.).

When in the above procedure 3-amino-5,5-diethyl-2-cyclohexen-1-one or 3-amino-5,5-dibutyl-2-cyclohexen-1-one are employed in place of 3-amino-5,5-dimethyl-2-cyclo-hexen-1-one the corresponding 5,6,7,8-tetrafluoro-2,2-diethylbenzo[2,1-b]quinolin-4-one and 5,6,7,8-tetrafluoro-2,2-dibutylbenzo[2,1-b]quinolin-4-one are obtained.

The antifungal activity of the polyfluorinated substituted quinoline mono- and dioxo compounds was determined according to the following procedure:

MICROBIOLOGICAL MINIMUM INHIBITORY CONCENTRATION TEST

MATERIALS

A. Test Organisms:
*Candida albicans* ATCC 10231
*Trichophyton mentagrophytes* ATCC 22839
*Microsporum canis* JJP #143
*Microsporum gypseum* ATCC 14683
*Trichophyton rubrum* ATCC 10218
*Epidermophyton floccosum* ATCC 15693

B. Culture Medium:
Mycophil Agar with low pH

PROCEDURE

A. Sample Preparation:
A 0.5 mg/ml stock solution of each compound was volumetrically prepared in an appropriate solvent From this stock, 1:2 serial dilutions were prepared in sterile distilled water. Two ml aliquots of the stock and serial dilutions were added to tubes containing 18 ml of mycophil agar (46°-50° C.). Mixtures were poured into square 100×15 mm petri dishes and allowed to solidify.

B. Inoculum Preparation:
All test organisms, except *Candida albicans* were harvested from six day mycophil agar slants. *Candida albicans* was diluted from a frozen stock culture. Inocula were diluted with sterile saline to contain approximately 1×10$^8$ CFUs per ml. Plate counts were performed on 1 ml of all inocula.

C. Sample Inoculation:
Each plate and appropriate solvent and unadulterated agar growth control was inoculated in duplicate with the inocula prepared above using a Steer's Replicator method.

Plates were then incubated at 32° C. Observations for growth were made at 24 and 48 hours and 7 days.

RESULTS

The minimal inhibitory concentration (MIC) is the lowest concentration of test material which completely inhibits growth. These MIC data are found in Table I.

TABLE I

| Antifungal Properties of Compounds I and II (MIC values in mcg/ml) | | |
| --- | --- | --- |
|  | I | II |
| Candida albicans | 50.0 | 50.0 |
| Trichophyton mentagrophytes | 25.0 | 6.2 |
| Trichophyton rubrum | 1.6 | 6.2 |
| Epidermophyton floccosum | 0.39 | 1.5 |
| Microsporum gypseum | 4.6 | 9.4 |
| Microsporum canis | 25.0 | 25.0 |

What is claimed is:

1. A compound of the formula:

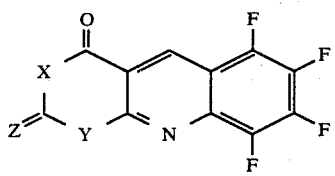

wherein X and Y are methylene or —NR
wherein R is lower alkyl, Z is oxo, thioxo, imino or —(R$_1$)$_2$
wherein R$_1$ is lower alkyl.

2. The compound of claim 1, which is 5,6,7,8-tetrafluoro-1,3-dimethylpyrimidino[6,5-b]quinolin-2,4-dione.

3. The compound of claim 1, which is 5,6,7,8-tetrafluoro-2,2-dimethylbenzo[2,1-b]quinolin-4-one.

4. The process for preparing a compound of the formula:

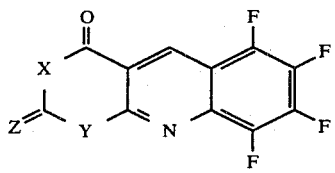

which comprises reacting pentafluorobenzaldehyde with an enaminone of the formula:

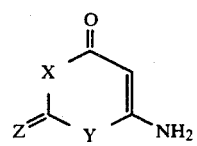

in an organic acid, wherein X and Y are methylene or —NR
wherein R is lower alkyl, Z is oxo, thioxo, imino or —(R$_1$)$_2$
wherein R$_1$ is lower alkyl.

5. The process according to claim 4, wherein the organic acid is selected from acetic acid, propionic acid and butyric acid.

6. The process according to claim 5, wherein the organic acid is glacial acetic acid.

* * * * *